US008753646B2

(12) United States Patent
Abe et al.

(10) Patent No.: US 8,753,646 B2
(45) Date of Patent: Jun. 17, 2014

(54) IPV-DPT VACCINE (75) Inventors: Shinobu Abe, Tokyo (JP); Bunsichi Simizu, Tokyo (JP)

(73) Assignees: Japan Poliomyelitis Research Institute, Tokyo (JP); Takeda Pharmaceutical Company Limited, Osaka (JP)

( * ) Notice: Subject to any disclaimer, the term of this patent is extended or adjusted under 35 U.S.C. 154(b) by 461 days.

(21) Appl. No.: 12/311,365

(22) PCT Filed: Sep. 28, 2007

(86) PCT No.: PCT/JP2007/069509
§ 371 (c)(1),
(2), (4) Date: Mar. 27, 2009

(87) PCT Pub. No.: WO2008/044661
PCT Pub. Date: Apr. 17, 2008

(65) Prior Publication Data
US 2010/0021497 A1    Jan. 28, 2010

(30) Foreign Application Priority Data
Sep. 29, 2006 (JP) ................. 2006-267439

(51) Int. Cl.
A61K 39/295 (2006.01)
C12N 7/00 (2006.01)
A61K 39/13 (2006.01)
A61K 39/02 (2006.01)
A61K 39/05 (2006.01)
A61K 39/12 (2006.01)
A61K 39/08 (2006.01)
A61K 39/00 (2006.01)

(52) U.S. Cl.
CPC ....... *A61K 39/12* (2013.01); *C12N 2770/32634* (2013.01); *C12N 7/00* (2013.01); *A61K 39/13* (2013.01); *A61K 39/099* (2013.01); *A61K 2039/5252* (2013.01); *A61K 39/05* (2013.01); *C12N 2770/32363* (2013.01); *C12N 270/32351* (2013.01); *A61K 39/08* (2013.01)
USPC .................................................... 424/201.1

(58) Field of Classification Search
None
See application file for complete search history.

(56) References Cited

U.S. PATENT DOCUMENTS

| 4,525,349 A | 6/1985 | Montagnon et al. |
| 6,696,065 B1 | 2/2004 | Fahim et al. |

FOREIGN PATENT DOCUMENTS

| CN | 1616095 A | 5/2005 |
| JP | 2000-504032 A | 4/2000 |
| JP | 3280675 B2 | 2/2002 |
| WO | WO 98/00167 A1 | 1/1998 |
| WO | WO 2007/007344 A1 | 1/2007 |
| WO | WO 2008/028957 A2 | 3/2008 |

OTHER PUBLICATIONS van Wezel (Rev. Inf. Dis., 6:S335-S340, 1984).*
Current Protocols in Molecular Biology (John Wiley & Sons, Inc., Chanda et al., 2003).*
Finch et al. (Appl. Environ. Microbiol., 57:3121-3126, 1991).*
Wong (SOP for BSL3 Sample preparation from Orhtopox Virus Using Rapigest; http://brcdownloads.vbi.vt.edu/brcdownloads/nav/organism/Monkeypox/post_genomic/pnnl/Prep-005-02_BSL3_Orthopox_Rapigest_Prep.doc; accessed Nov. 14, 2011).*
Pavlov (Can. J. Microbiol., 52:717-723, 2006).*
Ada (Overview of Vaccines, from Methods in Molecular Medicine, vol. 87, Vaccine Protocols 2nd Ed., Humana Press, 2003).*
Supplementary European Search Report dated Jul. 30, 2010, in corresponding EP 07829247.1, 6 pages.
Diez-Domingo et al., "Immunogenicity and Reactogenicity of a Combined Adsorbed Tetanus Toxoid, Low Dose Diphtheria Toxoid, Five Component Acellular Pertussis and Inactivated Polio Vaccine in Six-Year-Old Children," The Pediatric Infectious Disease Journal, Mar. 2005, 24(3):219-224.
Merten et al., "The new medium MDSS2N, free of any animal protein supports cell growth and production of various viruses," Cytotechnology, May 1999, 30(1-3):191-201.
Office Action dated Aug. 21, 2009 in corresponding Singapore application 0901814-4, 10 pages.
Drucker et al., "Evaluation of a new combined inactivated DPT-polio vaccine," Developments in Biological Standardization, 1986, 65: 145-151.
Montagnon et al., "Thousand litre scale microcarrier culture of vero cells for killed polio virus vaccine. Promising Results," Developments in Biological Standardization, 1983, 55:37-42.
Doi et al., "Progress with Inactivated Poliovirus Vaccines Derived from the Sabin Strains," Dev. Biol., Basel, Karger, 2001, 105:163-169.
Hashizume, "IPV Developed in Japan and Its Role in Eradication of Polio," reprint from Clinical Virology supplement, Dec. 30, 2002, Japanese Society of Clinical Virology, 30(5):336-343, with English translation, 15 pages.
Lindner et al., "Subpassaging cells on microcarriers: the importance for scaling up to production," Develop. Biol. Standard, 1987, 66:299-305.
Lindskog et al., "Alternatives for harvesting cells grown on microcarriers: effects on subsequent attachment and growth," Develop. Biol. Standard, 1987, 66:307-313.
Merten et al., "Evaluation of the serum-free medium MDSS2 for the production of poliovirus on Vero cells in bioreactors," Cycotechnology, 1997, 25:35-44.
Microcarrier Cell Culture Principles & Methods, Pharmacia Biotech, (Continued)

*Primary Examiner* — Brian J Gangle
(74) *Attorney, Agent, or Firm* — Foley & Lardner LLP (57) ABSTRACT

The invention provides a process for producing a combined vaccine containing an inactivated Sabin strain of poliovirus, a *Bordetella pertussis* protective antigen, a diphtheria toxoid and a tetanus toxoid, the process including a step of producing a high-titer Sabin strain poliovirus. The inventive process for producing a combined vaccine, including a step of culturing, in the presence of from about 4 g/L to about 6 g/L of a microcarrier, Vero cells to be inoculated with a Sabin strain of poliovirus, is useful as a process for efficiently producing a combined vaccine containing an inactivated Sabin strain of poliovirus.

10 Claims, 1 Drawing Sheet

(56) References Cited

OTHER PUBLICATIONS

"3.4.3 Concentration of microcarriers," 1988, 48-48, with English translation, 2 pages.

Montagnon et al. "The large-scale cultivation of vero cells in microcarrier culture for virus vaccine production preliminary results for killed poliovirus vaccine," Develop. Biol. Standard, 1981, 47:55-64.

Simizu et al., "Development of inactivated poliovirus vaccine derived from Sabin strains," Biologicals, 2006, 34:151-154.

Simizu, B., "Development of Sabin-IPV," Polio Vaccine: The first 50 Years and Beyond, Toronto, Canada, Jun. 5-7, 2005, 27 pages.

Wu et al., "Optimization of microcarrier cell culture process for the inactivated enterovirus type 71 vaccine development," Vaccine, 2004, 22:3858-3864.

* cited by examiner

IPV-DPT VACCINE

TECHNICAL FIELD

The present invention relates to a combined vaccine, particularly a combined vaccine containing an inactivated Sabin strain of poliovirus (sIPV), and to a method of preparation thereof

BACKGROUND ART

Polio is an infectious disease caused by a poliovirus. Polioviruses infect human by an oral route, proliferate in the intestinal tract, and enter the central nervous system through the blood. The proliferation within large motor neutrons of polioviruses that have entered the central nervous system causes neuronal degeneration and necrosis, triggering acute flaccid paralysis in the limbs. Moreover, when the poliovirus affects the medullary respiratory center, death from respiratory paralysis may result. Polio vaccines are widely used to suppress the onset of polio which triggers such severe symptoms.

Two types of polio vaccines are used: oral live polio vaccines and inactivated polio vaccines. Oral live polio vaccines are vaccines which use attenuated strains of poliovirus (Sabin strains). Attenuated strains of poliovirus that administered orally cause normal infections. Polioviruses from oral live polio vaccines grow well in the intestines, resulting in the formation of localized immunity within the intestines. In addition, when polioviruses from an oral live polio vaccine enter the blood and cause viremia, this also stimulates the production of antibodies within the blood. However, because the ability of attenuated strains of polioviruses to proliferate within the central nervous system is very weak, they generally do not cause paralysis. In the body of the inoculee, polioviruses from the oral live polio vaccine multiply and are excreted in the stools about 4 to 6 weeks following inoculation. The excreted viruses will infect people around the inoculee who have a weak immunity or no immunity to polio, conferring immunity or exhibiting a potentiating effect in the same way as in the inoculee.

However, in the course of repeated growth within the body of the inoculee or in the course of repeated growth in the body of a person infected by excreted viruses, an attenuated strain of poliovirus from an oral live polio vaccine sometimes gives rise to mutations in a highly virulent direction. In very rare instances, such mutants cause vaccine-associated paralysis.

An inactivated polio vaccine is a vaccine which has lost its infectiousness by inactivation of the poliovirus with formalin. Because an inactivated polio vaccine neither multiplies within the body of the inoculee nor infects people around the inoculee, it will not cause vaccine-associated paralysis. Highly virulent strains have hitherto been used to prepare inactivated polio vaccines, but advances have also been made recently in the development of attenuated strains (Sabin strains) (*Biologicals* 34, 151-154 (2006); *Dev. Bil. Basel. Karger* 105, 163-169 (2001), *Clinical Virology* 30, No. 5, 336-343 (December 2002)). The somewhat poorer growth of attenuated strains (Sabin strains) than highly virulent strains has been regarded as a drawback.

Vaccines which contain a *Bordetella pertussis* protective antigen, a diphtheria toxoid and a tetanus toxoid are widely used as diphtheria-tetanus-pertussis combined vaccines.

Polyvalent vaccines composed of an acellular pertussis vaccine, a diphtheria toxoid, a tetanus toxoid and inactivated poliovirus are known (Published Japanese Translation of a PCT Application No. 2000-504032).

Vero cells are passage cells from the kidneys of green monkeys. Because these cells have a broad sensitivity to various types of viruses, they are widely used in virus cultivation. A method for preparing an enterovirus type 71 vaccine that been reported in the literature includes culturing Vero cells on a microcarrier and using the cultured Vero cells to grow enterovirus 71 ("Optimization of microcarrier cell culture process for the inactivated enterovirus type 71 vaccine development," by Suh-Chin Wu, et al.: *Vaccine* 22, 3858-3864 (2004)). General cell culturing conditions using a microcarrier have also been described (Microcarrier cell culture principles & methods: Pharmacia LKB, Biotechnology, 1988).

DISCLOSURE OF THE INVENTION

Under such circumstances, there has existed a desire for a process for producing a combined vaccine containing an inactivated Sabin strain of poliovirus (sIPV), and also containing a *B. pertussis* protective antigen, a diphtheria toxoid and a tetanus toxoid (DPT), which process includes the step of preparing a high-titer Sabin strain poliovirus.

The inventors have conducted extensive investigations in order to resolve the above problem. As a result, the inventors have discovered that a high-titer Sabin strain poliovirus can be prepared by culturing, in the presence of from about 4 g/L to about 6 g/L of a microcarrier, Vero cells inoculated with a Sabin strain of poliovirus. After conducting repeated investigations based on these findings, the inventors ultimately arrived at the present invention.

The present invention thus provides such as:

(1) A process for preparing a combined vaccine containing
   (A) an inactivated Sabin strain of poliovirus,
   (B) a *Bordetella pertussis* protective antigen,
   (C) a diphtheria toxoid, and
   (D) a tetanus toxoid,
the process comprising (a) a step of culturing, in the presence of from about 4 g/L to about 6 g/L of a microcarrier, Vero cells to be inoculated with a Sabin strain of poliovirus.

(2) The process according to (1) above, further comprising:
   (b) a step of infecting the Vero cells with a Sabin strain of poliovirus;
   (c) a step of allowing the poliovirus to proliferate;
   (d) a step of recovering a virus fluid containing the poliovirus; and
   (e) a step of inactivating the poliovirus.

(3) The process according to (1) above, wherein the microcarrier has a concentration of about 5 g/L.

(4) The process according to (1) above, wherein the microcarrier is a dextran microcarrier.

(5) The process according to (1) above, wherein the step growing the Vero cell (step (a)) is carried out on a scale of at least about 3 liters.

(6) The process according to (1) above, wherein the step of growing the Vero cell (step (a)) is carried out on a scale of at least about 30 liters.

(7) The process according to (2) above, further comprising (d-2) a step of purifying the virus fluid.

(8) The process according to (7) above, wherein the purifying step (step (d-2)) comprises:
   (i) forming the virus fluid recovered in step (d) into a pellet by ultracentrifugation;
   (ii) sonicating a re-suspension of the pellet; and
   (iii) purifying by column chromatography.

(9) The process according to (8) above, wherein the purification by column chromatography (iii) is carried out one time only.

(10) A vaccine prepared by the process according to (1) above.
(11) The process of (1) above, wherein the step of culturing the Vero cell (step (a)) is carried out on a scale of at least about 3 liters.
(12) The process of (1) above, wherein the step of culturing the Vero cell (step (a)) is carried out on a scale of at least about 30 liters.

By culturing, in the presence of from about 4 g/L to about 6 g/L of a microcarrier, the Vero cells to be inoculated with a Sabin strain of poliovirus, it is possible to obtain high-titer Sabin strain poliovirus. By using the high-titer Sabin strain poliovirus, an inactivated Sabin strain poliovirus can be efficiently produced. Therefore, a process for producing a combined vaccine which includes the step of culturing, in the presence of from about 4 g/L to about 6 g/L of a microcarrier, Vero cells to be inoculated with a Sabin strain of poliovirus (the production process of the present invention) is useful as a process for the efficient production of combined vaccines containing an inactivated Sabin strain of poliovirus.

The present invention provides a process for producing a combined vaccine containing an inactivated Sabin strain of poliovirus (sIPV) together with a *B. pertussis* protective antigen, a diphtheria toxoid and a tetanus toxoid (DPT), which process includes the step of producing a high-titer Sabin strain of poliovirus.

The invention is described more fully below.

1. Inactivated Sabin Strain Poliovirus
(1) Sabin Strain Poliovirus

In the present specification, "Sabin strain of poliovirus" refers to a poliovirus strain derived from an attenuated strain of poliovirus isolated by Dr. Albert B. Sabin (see, for example, Sabin, A B, Boulger, L R: "History of Sabin attenuated poliovirus oral live vaccine strains," *J. Biol. Standard* 1, 115-118 (1973)).

Sabin strain polioviruses include Sabin type I strains of poliovirus, Sabin type II strains of poliovirus and Sabin type III strains of poliovirus. Examples of Sabin type I strains of poliovirus include the strains LSc and 2ab. Examples of Sabin type II strains of poliovirus include the strains P712, Ch and 2ab. Examples of Sabin type III strains of poliovirus include the strains Leon and $12a_1b$.

(2) Inactivation

In the present specification, virus "inactivation" refers to eliminating the infectious ability of a virus. Methods of inactivation include, but are not limited to, physical methods (e.g., methods involving the use of x-ray irradiation, heat or ultrasound) and chemical methods (e.g., methods involving the use of formalin, mercury, alcohol or chlorine).

Poliovirus inactivation may be carried out by a known method (see, for example, *Biologicals* 34, 151-154 (2006)). For instance, inactivation may be carried out by treating the poliovirus with formalin.

(3) Immunogenicity of Inactivated Sabin Strains of Poliovirus

Two viral antigens known as D antigens and C antigens are generally present in admixture within inactivated Sabin strains of poliovirus. D antigens are complete viral particles. Antibodies to D antigens have the ability to neutralize the infectiousness of live viruses, and function as protective antibodies. C antigens, called defective particles, are particles missing the core nucleic acid RNA and part of the viral proteins of a complete viral particle; these particles are hollow at the center. Antibodies to C antigens have little or no ability to neutralize the infectiousness of live viruses. Therefore, when an inactivated Sabin strain of poliovirus is to be used as a vaccine, the D antigens are required.

There are three types of polioviruses: type I, type II and type III. The immunity to poliovirus infection is specific to the three virus types—type I, type II and type III; what cross-immunity may exist between types is minimal. The D antigens of inactivated type I, type II and type III Sabin strains of poliovirus have immunogenicities capable of producing neutralizing antibodies for, respectively, type I, type II and type III wild strains (highly virulent) of poliovirus. The immunogenicities of the D antigens of inactivated Sabin strains of poliovirus differ for each of types I, II and III; hence, the amount of D antigen required to produce enough antibody to neutralize type I, type II and type III wild strains (highly virulent) of poliovirus differs according to the virus type.

As mentioned above, there are three types of polioviruses—type I, type II and type III, each of which causes the same polio. Therefore, when an inactivated Sabin strain of poliovirus is used as a vaccine (inactivated polio vaccine), it must have an immunogenicity capable of producing sufficient antibodies to neutralize wild strains (highly virulent strains) of polioviruses of each of types I, II and III. Moreover, it is desirable for the immunogenicity to be close to the immunogenicity of the inactivated polio vaccines from highly virulent strains that have hitherto been used. To exhibit such an immunogenicity, the vaccine preferably contains type I, type II and type III inactivated Sabin strains of poliovirus in a proportion, by weight of the respective D antigens, of preferably (2 to 4):(80 to 120):(80 to 120), and most preferably (about 3):(about 100):(about 100). The inactivated Sabin strains of poliovirus used in the present invention, by including types I, II and III in a specific proportion like the foregoing, exhibits an immunogenicity similar to that of inactivated polio vaccines from highly virulent strains (e.g., the Sauk vaccine).

2. Production of Inactivated Sabin Strains of Poliovirus

Inactivated Sabin strains of poliovirus suitable for use in the present invention can be produced by the method described below.

First, Vero cells are cultured in the presence of from about 4 g/L to about 6 g/L of microcarrier, thereby giving cells for culturing polioviruses. The resulting poliovirus culturing cells are inoculated with seed viruses (Sabin strain polioviruses) and the viruses are cultured, yielding Sabin strain polioviruses that have proliferated. The resulting Sabin strain polioviruses are inactivated to give inactivated Sabin strain polioviruses. Inactivated Sabin strain polioviruses can be obtained which correspond to the seed viruses used (Sabin type I strains, Sabin type II strains or Sabin type III strains). The viruses may be concentrated and/or purified before or after virus inactivation.

As mentioned above, the inactivated polio vaccine must have an immunogenicity capable of producing sufficient antibodies to neutralize wild strains (highly virulent strains) of each of types I, II and III. However, the D antigens of inactivated poliovirus Sabin strains have immunogenicities that differ between types I, II and III. Accordingly, inactivated polio vaccine possessing an immunogenicity capable of producing sufficient antibodies to neutralize wild strains (highly virulent strains) of each of types I, II and III can be obtained by adjusting the amounts of type I, type II and type III inactivated polioviruses contained.

(Vero Cells)

Vero cells are passage cells from the kidneys of green monkeys (*Cercopithecus aethiops*), and are deposited with the American Type Culture Collection (ATCC). Vero cells are widely used to culture viruses because they exhibit a fibroblastic morphology, have a broad sensitivity to various types of viruses and are easy to maintain as passage cells. Vero cells that are known to be available from ATCC include ATCC Nos. CCL-81 and CRL-1587.

(Microcarrier)

In this specification, "microcarrier" refers to a carrier that has surfaces to which cells adhere and enables cell cultivation to be carried out in a suspended state within a liquid medium. The microcarrier is not subject to any particular limitation with regard to material, shape and size, provided it is a carrier to the surface of which cells adhere and which enables cell cultivation to be carried out in a suspended state within a liquid medium.

Examples of the microcarrier material include dextran, gelatin, collagen, polystyrene, polyethylene, polyacrylamide, glass and cellulose. Dextran is preferred as the microcarrier material.

Examples of the microcarrier shape include spherical (beads) and discoidal shapes. The microcarrier preferably has a spherical shape.

The spherical microcarrier has a size of, for example, from about 0.01 to about 1 mm, preferably from about 0.05 to about 0.5 mm, and more preferably from about 0.1 to about 0.3 mm.

The microcarrier may be porous.

Examples of dextran spherical microcarriers that may be used in the present invention include CYTODEX 1 (trade name), CYTODEX 3 (trade name) and CYTOPORE (trade name) (all products of GE Healthcare Biosciences). Examples of discoidal microcarriers include CYTOLINE 1 (trade name) and CYTOLINE 2 (trade name) (both products of GE Healthcare Biosciences). Examples of porous microcarriers include CYTOPORE (trade name), CYTOLINE 1 (trade name) and CYTOLINE 2 (trade name) (all products of GE Healthcare Biosciences). The microcarrier used in the present invention is most preferably a spherical dextran microcarrier. The spherical dextran microcarrier is preferably CYTODEX 1 (trade name), CYTODEX 3 (trade name) or CYTOPORE (trade name), more preferably CYTODEX 1 (trade name) or CYTODEX 3 (trade name), and most preferably CYTODEX 1 (trade name).

(Vero Cell Cultivation)

In the present invention, the Vero cells are grown by cultivation in the presence of from about 4 g/L to about 6 g/L of microcarrier. The microcarrier concentration is preferably from about 4.5 g/L to about 5.5 g/L, and more preferably about 5 g/L.

The above-described Vero cell growing step is carried out on a scale, in terms of the liquid volume, of preferably at least 3 liters, more preferably at least 30 liters, and most preferably at least 150 liters. The Vero cell growing step is carried out on a scale of generally not more than 1,000 liters.

When the Vero cells are cultivated in the presence of a microcarrier, the culture medium used may be, for example, ME medium (*Science*, 122, 501 (1952)), DME medium (*Virology*, 8, 396 (1959)), RPMI 1640 medium (*The Journal of the American Medical Association*, 199, 519 (1967)) or 199 medium (*Proceedings of the Society for the Biological Medicine*, 73, 1 (1950)), which contain from about 5 to about 20 vol % of calf serum or fetal bovine serum. The culture medium is preferably a DME medium, more preferably a DME medium containing calf serum, and most preferably a DME medium containing about 5 vol % of calf serum. The medium may, if necessary, be changed during the period of cell cultivation. The pH is preferably from about 6 to about 8, more preferably from about 6.5 to about 7.5, and most preferably about 7. Cultivation is typically carried out at from about 35° C. to about 40° C. for a period of from about 5 to 9 days. If necessary, aeration and stirring may be carried out during cultivation. The dissolved oxygen concentration (DO) at the time of cell cultivation is preferably from about 60 to about 90%, more preferably from about 70 to about 80%, and most preferably about 75%.

The number of Vero cells in the medium at the start of cultivation in the presence of the microcarrier (starting number of cells) may be set as appropriate for such factors as the type of medium, the type of microcarrier, the scale of cultivation. The starting number of cells is preferably from $2\times10^4$ cells/mL to $10\times10^5$ cells/mL, and most preferably from $2\times10^5$ cells/mL to $10\times10^5$ cells/mL.

(Poliovirus Cultivation)

Poliovirus cultivation may be carried out by inoculating and thus infecting the cultured Vero cells with a Sabin strain of poliovirus (seed virus), and culturing the poliovirus within the cells. Cultivation of the infected cells may be carried out in the same way as the above-described Vero cell cultivation. The medium used for poliovirus cultivation is preferably a 199 medium, more preferably a 199 medium containing sodium bicarbonate, and most preferably a 199 medium containing 0.3 w/v % of sodium carbonate.

The incubation temperature during virus cultivation is preferably from about 30° C. to about 38° C., more preferably from about 32° C. to about 36° C., and most preferably from about 33° C. to about 35° C. The virus cultivation period is preferably from about 1 to about 5 days, more preferably from about 2 to about 4 days, and most preferably about 3 days. Virus cultivation may be brought to an end using cytopathic effects by the poliovirus (rounding of the poliovirus-infected cells and detachment of the cells from the microcarrier) as the indicator.

A Sabin strain of poliovirus that has been cultivated using green monkey primary-cultured kidney cells may be employed as the seed virus.

(Recovery of Poliovirus-Containing Virus Fluid)

Following the completion of virus cultivation, the microcarrier is removed and the virus fluid containing the poliovirus (sometimes referred to herein as the "poliovirus fluid") is recovered.

Removal of the microcarrier may be carried out by means of, for example, a Teflon mesh (such as one having a pore size of 120 μm). Because polioviruses remain present (attached)

to the microcarrier left on the mesh, these remaining polioviruses may be recovered by rinsing with, for example, the virus culture medium.

The resulting poliovirus fluid may be filtered using a filter membrane (e.g., a 0.2 μm filter membrane) or the like to remove cell debris.

The poliovirus fluid may be concentrated and/or purified before or after inactivation.

Illustrative examples of the method of concentration include ultrafiltration, ultracentrifugation and dialysis. The method of concentration is preferably ultrafiltration or ultracentrifugation. It is more preferable to carry out both ultrafiltration and ultracentrifugation, and even more preferable to carry out ultrafiltration followed by ultracentrifugation.

The membrane used in ultrafiltration may be an ultrafiltration membrane commonly employed for concentrating viruses. The ultrafiltration membrane has a molecular weight cutoff which is preferably about 100 kDa. The ultrafiltration membrane is preferably made of a material such as polyether sulfone.

Concentration of the poliovirus by ultracentrifugation may be carried out by subjecting the poliovirus fluid to 4 hours of centrifugation at 4° C. and 100,000 g to form a pellet. The pellet may be re-suspended in, for example, a phosphate buffer. It is also possible to break up the mass of aggregated viruses by sonicating the pellet re-suspension. Sonication may be carried out using a commercially available apparatus, such as Insonator Model 200M (Kubota). The sonication conditions should be sufficient to break up the mass of aggregated viruses, and may be selected as appropriate for such factors as the vessel used in sonication, the ultrasound output, and the concentration of the re-suspension. Sonication conditions are exemplified by treatment at 200 W for a period of from 3 to 10 minutes. Even when such sonication is carried out, the Sabin strain of poliovirus does not lose its immunogenicity, enabling it to be advantageously used as a poliovirus vaccine.

Methods of purification include, but are not limited to, methods which utilize physical characteristics of the substance being purified, such as size, density and sedimentation coefficient, and methods which utilize chemical or physicochemical reactions (e.g., adsorption-desorption). Illustrative examples of methods of purification include density-gradient centrifugation, filtration (including ultrafiltration), ion-exchange column chromatography, affinity chromatography, gel filtration chromatography and salting out. The method of purification is preferably column chromatography, more preferably ion-exchange column chromatography, and most preferably DEAE-ion-exchange column chromatography. The number of times purification is carried out by column chromatography is not subject to any particular limitation. That is, purification by column chromatography may be carried out repeatedly until the required purity is achieved. However, from the standpoint of production efficiency and other considerations, it is preferable to carry out such purification in as few steps as possible.

Concentration and purification are preferably carried out by forming the poliovirus fluid into a pellet by ultracentrifugation, sonicating a re-suspension of the resulting pellet, then purifying by column chromatography. In addition, from the standpoint of production efficiency, it is preferable to carry out purification by column chromatography one time only. By carrying out formation of the poliovirus fluid into a pellet by ultracentrifugation, sonication of a re-suspension of the pellet and purification by column chromatography one time only, the poliovirus fluid can be both efficiently and adequately concentrated and purified.

(Inactivation of Poliovirus)

Inactivation of the poliovirus may be carried out by a commonly employed method. Specifically, the poliovirus may be inactivated by adding an inactivator to the poliovirus fluid and thereby effecting a reaction between the poliovirus and the inactivator. The inactivator is preferably formalin. The inactivation conditions are not subject to any particular limitation, so long as the poliovirus is inactivated. To avoid the residual presence of insufficiently inactivated polioviruses, the period of inactivation treatment is generally from about 2 to about 4 times, preferably from about 2.5 to about 3.5 times, and more preferably about 3 times, the length of the period for which poliovirus inactivation has been confirmed.

For example, when formalin is used as the inactivator, the amount of addition is preferably from about 0.001 to about 0.1 w/v %, more preferably from about 0.005 to about 0.05 w/v %, and most preferably about 0.01 w/v %. The inactivation temperature is most preferably about 37° C. The inactivation period may vary also depending on the type of inactivator, the concentration of the inactivator, and the inactivation temperature. For example, when about 0.01 w/v % of formalin is used as the inactivator and the inactivation temperature is about 37° C., the inactivation period is preferably from about 8 to about 16 days, more preferably from about 10 to about 14 days, and most preferably about 12 days. When about 0.01 w/v % of formalin is used and the inactivation time is about 37° C., Sabin strain polioviruses are generally inactivated within 4 days.

3. Diphtheria Toxoid, *B. pertussis* Protective Antigen, and Tetanus Toxoid (DPT)

The *B. pertussis* protective antigen, diphtheria toxoid and tetanus toxoid used in the present invention are not subject to any particular limitation.

The *B. pertussis* protective antigen, diphtheria toxoid and tetanus toxoid are commercially available as diphtheria-pertussis-tetanus combined vaccines (such as those manufactured by Takeda Chemical Industries, Ltd., the Research Foundation for Microbial Diseases of Osaka University (Biken), and the Chemo-Sero-Therapeutic Research Institute (Kaketsuken)). Alternatively, the *B. pertussis* protective antigen, diphtheria toxoid and tetanus toxoid can be obtained by known methods. Specifically, the *B. pertussis* protective antigen may be obtained by, for example, extracting, isolating and purifying the phylactic antigen fraction from a culture broth of strains of phase I *B. pertussis* (Tohama strain) using a physicochemical method such as ammonium sulfate fractionation/sucrose density gradient centrifugal fractionation, then attenuating the remaining virulence with formalin. The diphtheria toxoid may be obtained by, for example, purifying and concentrating the toxin produced by *Corynebacterium diphtheriae* (Park-Williams No. 8 strain) using a physicochemical method such as column chromatography, followed by detoxification with formalin. The tetanus toxoid may be obtained by, for example, purifying and concentrating the toxin produced by *Clostridium tetani* (Harvard strain) using a physicochemical method such as column chromatography, followed by detoxification with formalin.

The *B. pertussis* protective antigen contains pertussis toxin (PT antigen), filamentous hemagglutinin (FHA antigen), outer membrane protein (69 KD antigen), and fimbriae (also called FB antigen, agglutinogen (FGG)). The *B. pertussis* protective antigen need not necessarily contain each of the above antigens, so long as it contains at least one, preferably at least two, and more preferably at least three of these antigens. Antibodies for these protective antigens protect the host from pertussis.

4. Combined Vaccine

The combined vaccine of the present invention contains inactivated Sabin strains of poliovirus, B. pertussis protective antigen, diphtheria toxoid and tetanus toxoid. As mentioned above, the B. pertussis protective antigen, diphtheria toxoid and tetanus toxoid are available commercially as diphtheria-tetanus-pertussis combined vaccines. Therefore, the combined vaccine of the present invention may also be prepared by mixing inactivated Sabin strains of poliovirus together with a diphtheria-tetanus-pertussis combined vaccine.

The inactivated Sabin strains of poliovirus may be prepared by mixing inactivated Sabin type I poliovirus strains, inactivated Sabin type II poliovirus strains, and inactivated Sabin type III poliovirus strains. As mentioned above, the inactivated Sabin strains of poliovirus contain the type I, type II and type III inactivated Sabin strains of poliovirus in a ratio, based on the amounts of the respective D antigens thereof, of preferably (2 to 4):(80 to 120):(80 to 120), and most preferably (about 3):(about 100):(about 100).

The B. pertussis protective antigen, diphtheria toxoid and tetanus toxoid may included within the combined vaccine of the invention in any amounts that are effective for preventing pertussis, diphtheria and tetanus. Specifically, these respective amounts may be the same as the corresponding amounts in the above-mentioned commercially available diphtheria-tetanus-pertussis combined vaccines. In cases where the immunogenicities of the B. pertussis protective antigen, diphtheria toxoid and/or tetanus toxoid are influenced by the inactivated Sabin strain of poliovirus and other ingredients, a combined vaccine effective for preventing each of the target illnesses may be produced by suitably adjusting the respective contents.

The combined vaccine of the invention may be produced and used by conventional means. Specifically, production and use may be carried out as described below.

The combined vaccine of the invention may be prepared as an injection by a conventional method. Such an injection is prepared in accordance with a method that is itself known to the art, such as dissolving, suspending or emulsifying the above substances in a sterile aqueous or oleaginous liquid commonly used in injections. Examples of aqueous liquids for injection which may be used include physiological saline and isotonic solutions containing glucose or some other adminiculum. The injectable solution that has been prepared is typically filled into a suitable ampule or syringe.

The combined vaccine of the invention may also optionally include pharmaceutical additives such as preservatives, antioxidants and chelating agents. Illustrative examples of preservatives include thimerosal and 2-phenoxyethanol. Illustrative examples of chelating agents include ethylenediaminetetraacetic acid and glycol ether diaminetetraacetic acid.

The combined vaccine of the invention may additionally contain adjuvants. Illustrative examples of adjuvants include aluminum hydroxide, aluminum phosphate and aluminum chloride.

In addition to the inactivated Sabin strain poliovirus, B. pertussis protective antigen, diphtheria toxoid and tetanus toxoid, the combined vaccine of the invention may also include other immunogenic ingredients. Illustrative examples of such immunogenic ingredients include immunogenic ingredients for viruses or bacteria other than poliovirus, B. pertussis, C. diphtheriae and C. tetani. Examples of such immunogenic ingredients include toxoids, attenuated viruses, inactivated viruses, proteins, peptides, polysaccharides, lipopolysaccharides, lipopeptides and combinations thereof. Examples of viruses and bacteria other than poliovirus, *B. pertussis, C. diphtheriae* and *C. tetani* include influenza viruses, measles virus, mumps virus, rubella virus, herpes virus, smallpox virus, rabies virus, human immune deficiency virus, hepatitis virus, *Diplococcus pneumoniae, Neisseria meningitidis*, typhoid bacillus and *Haemophilus influenzae* Type b.

The combined vaccine of the present invention may be administered parenterally, such as by subcutaneous injection or intramuscular injection, and preferably by subcutaneous injection.

The amount of a single dose of the combined vaccine of the invention may be suitably selected according to various conditions, such as the age and body weight of the target vaccinee. Specifically, a single dose may contain, for example, at least 4 international units of the *B. pertussis* protective antigen, about 15 Lf of diphtheria toxoid, about 2.5 Lf of tetanus toxoid, about 2 to about 4 units (preferably about 3 units) of inactivated Sabin type I poliovirus (D antigen basis), about 80 to about 120 units (preferably about 100 units) of inactivated Sabin type II poliovirus (D antigen basis), and from about 80 to about 120 units (preferably about 100 units) of inactivated Sabin type III poliovirus (D antigen basis).

The number of times the combined vaccine of the invention is administered as an initial immunization may be, for example, two or three doses at 3- to 8-week intervals. When the inventive combined vaccine is administered twice as an initial immunization, it is desirable to administer also a diphtheria-pertussis-tetanus combined vaccine (DPT vaccine) at an interval of 3 to 8 weeks. As a booster immunization, the inventive combined vaccine may be given one more time at an interval of at least 6 months following initial immunization (e.g., from 12 to 18 months following the end of initial immunization).

EXAMPLES

The present invention is illustrated more fully below by way of examples, although the examples do not limit the scope of the invention.

Reference Example 1

Establishing a Manufacturer's Working Cell Bank for Polio Vaccine Viruses

A bank of preserved cells for the production of polio vaccine viruses was prepared by the procedure described below from Vero cells acquired from ATCC.

(i) Preparation of Master Cell Bank (MCB)

Frozen cells in an ampule received from ATCC (CCL 81 Vero, F-6573; passage number, 124) were thawed, and transferred to an empty 4-ounce flask (a flask having a capacity of 154 mL and a cell growth surface area of 54 $cm^2$). Fifteen milliliters of a cell growth medium (DME (Dulbecco's Modified Eagle's Medium; Sigma, catalog No. D5523) containing 5 vol % calf serum, 0.075% sodium bicarbonate, 20 μg/mL erythromycin and 100 μg/mL kanamycin (final concentrations)) was added dropwise to the cell-containing 4-ounce flask over a period of about 5 minutes. The flask containing the cells and the cell growth medium was static cultured at 36° C. (one 4-ounce flask, passage 125). The next morning, the cell growth culture was replaced with 15 mL of fresh culture and static culturing was again carried out at 36° C. On day 6 following the start of the static culture, a subculture was carried out (from one 4-ounce flask to four 4-ounce flasks, passage 126). The subculture method was carried out as follows.

Subculture Method
(1) Discard culture broth.
(2) Place 5 mL of 0.25% trypsin solution for subculturing in 4-ounce flask.
(3) Immerse cell surfaces for about 1 minute, then discard 0.25% trypsin solution for subculturing.
(4) Place 4-ounce flask at rest at 36° C., and wait for cells to detach from glass surface.
(5) When cells have begun to detach, add 5 mL of cell growth medium and induce all cells to detach by pipetting.
(6) Suspend cells uniformly by further pipetting, then transfer cell growth medium to a centrifuge tube.
(7) Centrifuge for 5 minutes at 600 rpm, discard supernatant, and uniformly suspend sedimented cells in about 8 mL of fresh cell growth medium by pipetting.
(8) Add 2 mL of cell suspension to each of four new 4-ounce flasks (in each of which 13 mL of fresh cell growth medium has been distributed).
(9) Place four 4-ounce flasks at rest at 36° C. and carry out cell cultivation.

The composition of the 0.25% trypsin solution for subculturing was as follows.
5% trypsin*[1], 50 mL/L
5% Polyvinyl pyrrolidone (90K), 20 mL/L
0.247 mol sodium edetate*[2], 56 mL/L
EK*[3], 2 mL/L
Trypsin diluting fluid*[4], 872 mL/L

*[1]: Trypsin from porcine pancreas and having an activity of 1:300 was used.
*[2]: The composition of 0.247 mol sodium edetate was as follows:
Sodium edetate-2Na.2H$_2$O, 91.95 g/L
NaOH, 9.88 g/L
*[3]: The composition of EK was as follows:
Erythromycin lactobionate, 10,000 μg/mL
Kanamycin sulfate, 50,000 μg/mL
*[4]: The composition of the trypsin diluting fluid was as follows:
NaCl, 8,000 mg/L
KCl, 400 mg/L
Na$_2$HPO$_4$.12H$_2$O, 150 mg/L
KH$_2$PO$_4$, 60 mg/L Subculturing was subsequently carried out by the same method (although, because the culture surface area is increased about 3- to 4-fold in a single passage, the culture bottles and the liquid volume handled differed) at 3- to 6-day intervals, thereby producing passage 129 cells (the passage number increases by one each time subculturing is carried out). The cultured passage 129 cells were trypsin treated in 33 SR flasks (Small Roux flasks: culture flasks having a volume of 727 mL and a cell growth surface area of 156 cm$^2$) in the same way as during subculturing and centrifugation was carried out, following which the sediment was re-suspended to a concentration of about $1.5\times10^7$ cells/mL in a cryopreserved medium (DME (Dulbecco's Modified Eagle's Medium; Sigma, Catalog No. D5523) containing 10% dimethyl sulfoxide (DMSO), 10 vol % calf serum, 0.075% sodium bicarbonate, 20 μg/mL erythromycin and 100 μg/mL kanamycin (final concentrations)). One milliliter of the above cell suspension was dispensed to an ampule, the temperature was lowered to −32° C. in a slow freezer (at a cooling rate of about 1° C./min), then transferred to liquid nitrogen and preserved. The passage 129 cells obtained as described above were used as the master cell bank (MCB).

(ii) Preparation of Manufacturer's Working Cell Bank (MWCB)

Using the Master Cell Bank (MCB) prepared and preserved in section (i) above, the steps from thawing of the cells in the ampule to growth by cell subculturing up to passage 134 were carried out in basically the same exact way as was used to prepare the Master Cell Bank (MCB) in (i) above (although, because the number of starting cells was higher, the amount of liquid handled and the type and number of culture flasks differed). The passage 134 cells were preserved in liquid nitrogen in the same way as the Master Cell Bank (MCB). The passage 134 cells thus obtained were used as a Manufacturer's Working Cell Bank (MWCB).

Example 1

Preparation of Cells for Production of Polio Vaccine Viruses (i) Static Cultivation Step One ampule of the Manufacturer's Working Cell Bank (MWCB) prepared and preserved in Reference Example 1 above (passage 134 cells) was thawed in the same way as in the preparation of the Master Cell Bank (MCB) and the Manufacturer's Working Cell Bank (MWCB) in Reference Example 1, and the cells were static cultured for 7 days (passage 135) in three LR flasks (Large Roux flasks, which are culture flasks having a capacity of about 1,540 mL and a cell growth surface area of about 274 cm$^2$). Subculturing was carried out until day 7 from the start of static culturing, following which the scale of cultivation was expanded to 18 LR flasks (passage 136) and static culturing was carried out. Static culturing and subculturing thereof were carried out by the same method as in the preparation of the Master Cell Bank (MCB) and the preparation of the Manufacturer's Working Cell Bank (MWCB) in Reference Example 1 above.

Next, 7 days of static culturing was carried out in a 40-tray Cell Factory (Nunc, Catalog No. 139446) (passage 137). Subculturing was then carried out on day 7 following the start of the static culture, in addition to which 7 days of static culturing was carried out in four 40-tray Cell Factories (passage 138).

(ii) Microcarrier Culturing Step

Next, the passage 138 cells obtained in the static culturing step in (i) above were trypsin treated and centrifuged in the same way as during subculturing in (i) above, and the sedimented cells were uniformly suspended by pipetting in 1,000 mL of a cell growth medium for microcarrier culturing (DME (Dulbecco's Modified Eagle's Medium; Sigma, Catalog No. D5523) containing 5 vol % calf serum (Thermo Trace), 0.11% sodium bicarbonate, 0.1% fructose, 20 μg/mL erythromycin, and 100 μg/mL kanamycin (final concentrations)). The cell suspension was swelled beforehand with phosphate buffered saline (PBS), then mixed with a microcarrier (CYTODEX 1 (trade name); GE Healthcare Biosciences) equilibrated with the cell growth medium for microcarrier culturing (5 g/L of CYTODEX 1 (trade name) was used, based on the weight prior to swelling), and culturing was carried out in three 50-liter culture vessels at 37° C., pH 7.15 and under stirring. Starting on day 2 of culturing, one-half of the cell growth medium was successively replaced once daily with fresh cell growth medium. The cells grown for 7 days were used as cells (passage 139) for the production of polio vaccine viruses.

Example 2

Production of Inactivated Polio Vaccine Type I (i) Virus Cultivation Step

Just prior to the inoculation of seed viruses into the cells for polio vaccine virus production obtained in Example 1 (passage 139), stirring was stopped and the cells were allowed to settle, then washed once using Earl's Balanced Salt Solution (EBSS) containing 0.075% sodium bicarbonate, 20 μg/mL erythromycin and 100 μg/mL of kanamycin (final concentrations). After removing the supernatant from the 5 mL of cell growth medium collected together with the microcarrier, the volume was again brought up to 5 mL by adding 0.25% trypsin solution, thereby detaching the cells from the beads and causing them to be suspended. The cell count was then determined, based on which the number of cells for the entire 50-liter culture vessel was estimated. Attenuated Sabin type I (LSc, 2ab strains) seed viruses were inoculated in a concentration of about $10^{-1}$ $CCID_{50}$ per cell. Following inoculation of the seed viruses, 50 L of a virus culture medium (M199 (Medium 199) containing 0.3% sodium bicarbonate, 20 μg/mL erythromycin and 100 μg/mL of kanamycin (final concentrations)) was immediately poured into the culture vessel. The seed viruses used were viruses that had been cultured beforehand at about 33.3° C. using African green monkey primary-cultured kidney cells, then packaged in small portions and cryopreserved at −70° C.

Virus cultivation was carried out at 34° C.±1° C. for 3 days. Using the cytopathic effects by the poliovirus (rounding of the poliovirus-infected cells, followed by detachment of the cells from the microcarrier) as the indicator, virus cultivation was brought to an end when from 95 to 100% of the cells had detached from the microcarrier. Following the completion of virus cultivation, the microcarrier was removed with a Teflon mesh (pore size, 120 μm), and the virus suspension was recovered. The microcarrier remaining on the mesh was washed once with about 3 L of virus culture medium per 50 L culture vessel. The resulting wash fluid was added to the recovered virus suspension, thereby giving a "Type I polio virus fluid."

(ii) Virus Concentration/Purification Step

About 150 L of the Type I poliovirus fluid obtained in (i) above was passed through a 0.2 μm filter membrane (Pall Corporation, SLK7002NRP) to remove cell debris. The filtrate was concentrated to 1.2 L with an ultrafiltration membrane (Sartorius, PESU (polyethersulfone) 100 kDa, $0.1m^2$, 3051466801E—SG). The concentrated virus fluid was formed into a pellet by 4 hours of ultracentrifugation at 6° C. and 100,000 g, and following which the pellet was re-suspended in 0.1 mol/L phosphate buffer (PB) (the pellet from one centrifuge tube (about 100 mL) was re-suspended in 5 mL of PB). The pellet re-suspension was shaken overnight at 4° C., then sonicated (Kubota, Insonator Model 200M) for 8 minutes at 200 W, thereby breaking up the mass of aggregated viruses. Next, after 30 minutes of centrifugation at 15,000 rpm, the supernatant was collected. The supernatant thus obtained was purified with DEAE SEPHAROSE CL-6B (trade name, GE Healthcare Biosciences; GE 17-0710-05). Phosphate buffer (PB), 0.1 mol/L, was used as the eluate. The absorbance at 280 nm was monitored and the first peak was recovered as "purified Type I poliovirus fluid." The absorbance at 260/280 nm for the sampled peak was calculated and confirmed to be greater than 1.5 (the 260/280 nm absorbance for complete poliovirus particles is from 1.6 to 1.7).

(iii) Inactivation Step

The purified type I poliovirus fluid obtained in (ii) above was diluted about 10-fold with a pre-inactivation diluting solution (M199 containing 5% aminoacetic acid (final concentration), but containing no calcium, magnesium, Phenol Red or sodium bicarbonate), passed through a 0.2 μm filter membrane (Pall Corporation, SLK7002NRP), and the mass of aggregated viruses was removed. Following preparation of the filtrate, inactivation was rapidly begun in such a way as to avoid aggregating of viruses again. One hour prior to the start of inactivation, the filtrate and formalin diluted to 1:200 were separately warmed at 37° C. While thoroughly stirring the filtrate, the formalin was added to a final concentration of 1:4,000, the mixture was warmed to 37° C., and inactivation was begun. During formalin treatment, virus inactivation was made to proceed uniformly by stirring the mixture twice daily—once in the first half of the day and once in the second half of the day. Anticipating that insufficiently inactivated viruses would adhere to the vessel stopper and to certain specific places within the vessel, the stopper was changed on days 2 and 4 following the start of inactivation, and the vessel itself was changed on day 6. In addition, given the possibility that the viruses would aggregate during the inactivation step, on day 6 of inactivation, filtration was carried out using a 0.2 μm filter membrane (Pall Corporation, SLK7002NRP). The formalin treatment step was brought to an end after 12 days. On day 12, free formalin in the formalin-treated virus fluid was neutralized with sodium sulfite (added to a concentration of 0.0264 mol/L), following which sodium edetate was added (0.0009 mol/L) as a stabilizer, thereby giving a bulk material of "inactivated type I polio vaccine."

(iv) The amount of D antigen is measured by an indirect ELISA method using antibodies having a high specificity to the type and the D antigen. The indirect ELISA method begins by coating a microplate with, as the primary antibody, a monoclonal antibody (mouse-derived) specific for D antigens of the same type as the antigen to be assayed. The antigen to be assayed is then diluted and placed thereon. Next, a rabbit polyclonal antibody of the same type as the antigen to be assayed is placed thereon as the secondary antibody, in addition to which HRPO-labeled anti-rabbit IgG antibody is placed thereon, effecting a reaction. Following the reaction, color development is carried out using an o-phenylenediamine solution, and the absorbance at 492 nm is measured. The amount of D antigen (assayed antigen) is determined by comparing the measured absorbance for the assayed antibody and the measured absorbance for a reference antigen by parallel-line quantitative analysis.

Example 3

Production of Inactivated Polio Vaccine Type II

Aside from using attenuated Sabin type II strains (P712, Ch, 2ab strains) instead of attenuated Sabin type I strains (LSc, 2ab strains), a bulk material of "inactivated type II polio vaccine" was produced in the same way as in Example 2.

Example 4

Production of Inactivated Polio Vaccine Type III

Aside from using attenuated Sabin type III strains (Leon, $12a_1b$ strains) instead of attenuated Sabin type I strains (LSc, 2ab strains), a bulk material of "inactivated type III polio vaccine" was produced in the same way as in Example 2.

Example 5

Production of *B. pertussis* Protective Antigen (1) Cultivation of *Bordetella Pertussis*

Strains of phase I *B. pertussis* (Tohama strain) were spin-cultured at 30 to 34° C. for 20 to 24 hours in a Cohen-Wheeler medium. The *B. pertussis* grown on the Cohen-Wheeler medium were then grown on a Stainer-Scholte medium at 30 to 34° C. for 48 to 68 hours.

The culture was concentrated to $1/10^{th}$ the original volume by ultracentrifugation, and the supernatant and bacterial cells were separated by centrifugal separation.

(2) Preparation of Pertussis Toxin

Next, 1 mol/L phosphate buffer (pH 8.0) was added to the supernatant obtained in (1) above so as to bring the volume up to $1/10^{th}$ the original volume, then a 25 w/v % calcium acetate solution was added to bring the concentration to from 0.1 to 2.0 w/v %, and a filtrate containing pertussis toxin (phylactic antigen) was obtained by filtration. The filtrate was passed through a column by SP column chromatography (equilibrated solution: 0.1 mol/L phosphate buffer (pH 6.0) and the adsorbed pertussis toxin was eluted with 0.415 mol/L phosphate buffer (pH 7.0), thereby fractionating a pertussis toxin-containing solution. Next, the pertussis toxin-containing solution was passed through a column by gel column chromatography (equilibrated solution: 0.025 mol/L sodium phosphate solution (pH 8.7) containing 0.25 mol/L sodium chloride), then filtered (pore size, 0.2 μm), giving a pure pertussis toxin (PT antigen) solution.

(3) Preparation of Filamentous Hemagglutinin

The bacterial cells isolated in (1) above were dispersed in a 0.05 mol/L phosphate buffer (pH 8.0) containing 1 mol/L sodium chloride, following which centrifugal separation was carried out to again separate the supernatant and the bacterial cells. A 25 w/v % calcium acetate solution was added to the re-separated supernatant to a concentration of from 0.1 to 2.0 w/v %, following which filtration was carried out, giving a solution containing filamentous hemagglutinin (phylactic antigen). The filtrate was concentrated with ammonium sulfate, then purified by density gradient centrifugation, thereby fractionating pure filamentous hemagglutinin (FHA antigen).

(4) Preparation of Outer Membrane Protein

The bacterial cells re-separated in (3) above were dispersed in a 0.01 mol/L phosphate buffer (pH 7.0) containing 0.145 mol/L of sodium chloride and heated at 60° C. for 90 minutes, following which the supernatant and bacterial cells were again re-separated by centrifugal separation. Next, 1 mol/L phosphate buffer (pH 8.0) was added to the again re-separated supernatant so as to bring the volume up to $1/10^{th}$, following which a 25 w/v % calcium acetate solution was added to concentrations of from 0.1 to 2.0 w/v % and filtration was carried out, thereby giving a filtrate containing outer membrane protein (phylactic antigen). The solution containing outer membrane protein (phylactic antigen) was subjected to SP column chromatography (equilibrated solution: 0.1 mol/L phosphate buffer (pH 6.0)), and the liquid that passed through the column was collected. Next, the liquid was passed through a column by gel column chromatography (equilibrated solution: 0.025 mol/L sodium phosphate solution (pH 8.7) containing 0.25 mol/L sodium phosphate), then filtered (pore size, 0.2 μm), thereby giving pure outer membrane protein (69 K antigen).

(5) Preparation of Fimbriae (Agglutinogen (AGG))

A 0.1 mol/L phosphate buffer (pH 8.0) containing 1 mol/L of sodium chloride was added to the residue left following collection of the outer membrane protein-containing solution in (4) above in an amount $1/10^{th}$ the amount of the supernatant, following which filtration was carried out, yielding a filtrate containing fimbriae (phylactic antigen). The resulting fimbriae-containing solution was concentrated with ammonium sulfate, then purified by density gradient centrifugation, thereby fractionating pure fimbriae (FB antigen).

(6) Preparation of Protective Antigen (Attenuation)

A solution containing the PT antigen, FHA antigen, 69 KD antigen and FB antigen obtained in sections (2) to (5) above mixed in such a way that the DPT combined vaccine prepared in Example 8 below will include antigen levels of 1.89 μg of PT antigen, 3.00 μg of FHA antigen, 0.76 μg of 69K antigen and 0.36 μg of FB antigen per 0.5 mL of vaccine was prepared as a pure phylactic antigen solution. Formalin (from 0.2 to 0.5 vol %) and, if necessary, lysine hydrochloride to a concentration of not more than 1 w/v % were added to the pure phylactic antigen solution, following which the solution was warmed at 37 to 41° C. for at least 7 days to effect attenuation, thereby giving a pertussis protective antigen solution. Excess formalin and lysine hydrochloride were removed by ultrafiltration, giving a pertussis protective antigen bulk material.

Example 6

Production of Diphtheria Toxoid (1) Cultivation of *Corynebacterium Diphtheriae*

*C. diphtheriae* (Park-Williams No. 8 strain) was cultured on Loeffler's medium at 32.0 to 34.0° C. for 5 days.

(2) Preparation of Diphtheria Toxin

Ammonium sulfate was added to the culture fluid obtained in (1) above, following which the supernatant was filtered (pore size, 0.45 μm). The resulting filtrate was passed through a column by phenyl hydrophobic column chromatography (equilibrated solution: 0.01 mol/L sodium phosphate solution (pH 6.5) containing 1.25 mol/L ammonium sulfate). The toxin solution thereby obtained was passed through a column by DEAE ion-exchange column chromatography (equilibrated solution: 0.01 mol/L phosphate buffer (pH 7.0)), then passed through a column by gel column chromatography (equilibrated solution: 0.1 mol/L phosphate buffer (pH 7.0) containing 0.145 mol/L sodium chloride), thereby fractionating the diphtheria toxin. This was used as a pure toxin solution.

(3) Conversion of Diphtheria Toxin to Toxoid

Next, lysine hydrochloride was added to the pure toxin solution obtained in above (2) to a concentration of not more than 1 w/v %, formalin was added to a concentration of 0.3 vol %, and the solution was warmed at 38.0 to 40.0° C. for 21 days, thereby converting the toxin to toxoid.

(4) Preparation of Diphtheria Toxoid

Following the conversion to toxoid in (3) above, excess formalin and lysine hydrochloride were removed by ultrafiltration, thereby giving a diphtheria toxoid.

Example 7

Production of Tetanus Toxoid (1) Cultivation of *Clostridium Tetani*

*C. tetani* (Harvard 47-A) was cultured in liver bouillon at 34.5° C. to 36.5° C. for 5 days.

(2) Preparation of Tetanus Toxin

Ammonium sulfate was added to the culture obtained in (1) above to a concentration of 1.25 mol/L per liter of the culture. Next, the culture was passed through a column by phenyl hydrophobic column chromatography (equilibrated solution:

0.01 mol/L sodium phosphate (pH 6.5) containing 1.25 mol/L ammonium sulfate). The resulting toxin solution was passed through a column by DEAE ion-exchange chromatography (equilibrated solution: 0.01 mol/L phosphate buffer (pH 7.5)), following which the solution was passed through a column by gel column chromatography (equilibrated solution: 0.004 mol/L phosphate buffer (pH 7.0) containing 0.145 mol/L sodium chloride), thereby fractionating the tetanus toxin. This was used as a pure toxin solution.

(3) Conversion of Tetanus Toxin to Toxoid

Next, formalin was added to the pure toxin solution obtained in above (2) to a concentration of 0.3 vol %, the pH was corrected to 7.0, and the solution was warmed at 39° C. for 15 to 23 days, thereby converting the toxin to toxoid.

(4) Preparation of Tetanus Toxoid

Following the conversion to toxoid in (3) above, excess formalin and lysine hydrochloride were removed by ultrafiltration, thereby giving a tetanus toxoid.

Example 8

Production of Combined Vaccine (i) Preparation of Combined Inactivated Polio Vaccine The bulk materials of inactivated polio vaccine type I, inactivated polio vaccine type II and inactivated polio vaccine type III obtained in Examples 2, 3 and 4 above were mixed with medium 199 (M199), 2-phenoxyethanol (final concentration, 0.5 vol %) and aluminum chloride (final concentration, 0.09 w/v %) in such a way as to set the relative levels of the respective D antigens to 3:100:100. The resulting mixture was adjusted to a pH of 7 with sodium hydroxide or hydrochloric acid, thereby giving a combined inactivated polio vaccine.

(ii) Production of DPT Combined Vaccine

The *B. pertussis* protective antigen, diphtheria toxoid and tetanus toxoid bulk materials obtained in Examples 5, 6 and 7 above were mixed with 199 medium (M199), 2-phenoxyethanol (final concentration, 0.5 vol %) and aluminum chloride (final concentration, 0.24 w/v %). The resulting mixture was adjusted to a pH of 7 with sodium hydroxide and hydrochloric acid, thereby giving a DPT combined vaccine.

(iii) Production of Combined Vaccine

The combined inactivated polio vaccine obtained in (i) above and the DPT combined vaccine obtained in (ii) above were mixed in equal amounts, thereby producing a combined vaccine.

Example 9

Stability of Combined Vaccine

The combined vaccine obtained in Example 8 was measured by carrying out an accelerated test at 25° C. The stability was evaluated by potency tests on each of the viruses.

(1) Potency Test of Precipitated Pure Pertussis Vaccine

A test specimen, a standard pertussis vaccine and *B. pertussis* strain 18323 are used. The test specimen and the standard vaccine are each diluted, from which dilutions of each in a total of at least 3 serial dilutions at suitable logarithmically equal intervals of 4-fold or more are then prepared. One group of at least sixteen 4-week-old mice is used for each dilution. Each animal is given 0.5 mL of dilution as a single intraperitoneal injection. Twenty-one days after the immune injections, 0.025 mL of a bacterial cell suspension for challenge is injected into the brain of each animal, following which the animals are observed for 14 days and the number of deaths is tallied. From statistical treatment and comparison of the test results, the test specimen must have a potency of at least 8 units/mL.

(2) Potency Test of Precipitated Diphtheria Toxoid

A test specimen, a control precipitated diphtheria toxoid and a suitable toxin solution are used. Dilution of the test specimen and the control is carried out with physiological saline; dilution of the toxin solution is carried out with a 0.017 mol/L phosphate buffer/sodium chloride solution (pH 7.0) containing 0.2 w/v % of gelatin. The test specimen and the control are each diluted, creating serial dilutions at logarithmically equal intervals. Using one group of at least ten 5-week-old mice for each dilution of the test specimen and the control, each animals is subcutaneously injected with 0.5 mL. Four to six weeks following the immune injections, blood is drawn from each animal, and the blood antitoxin titer is measured. From statistical treatment and comparison of the test results, the test specimen must have a potency of at least 47 units/mL.

(3) Potency Test of Precipitated Tetanus Toxoid

A test specimen, a control precipitated tetanus toxoid and a suitable toxin solution are used. Dilution of the test specimen and the control is carried out with physiological saline; dilution of the toxin solution is carried out with a 0.017 mol/L phosphate buffer/sodium chloride solution (pH 7.0) containing 0.2 w/v % of gelatin. The test specimen and the control are each diluted, creating serial dilutions at logarithmically equal intervals. Using one group of at least ten 5-week-old mice for each dilution of the test specimen and the control, each animal is given a single subcutaneous injection of 0.5 mL. Four to six weeks following the immune injections, each mouse is challenged with about 100 $LD_{50}$ of toxin and observed for 4 days. From statistical treatment and comparison of the test results, the test specimen must have a potency of at least 27 units/mL.

(4) Rat Immunogenicity Test

A test specimen, a control for an IPV potency test, standard sera for each type, and Sabin strains of poliovirus (types I, II and III) for neutralization test challenges are used. The test specimen and control are each diluted, creating dilutions at logarithmically equal intervals. One group of at least ten Wister 8-week-old female rats is used for each dilution. Each animal is intramuscularly inoculated with 0.5 mL in the femoral region of the hind leg. Twenty-one days following inoculation, blood is drawn individually from each animal and the serum is collected then heated at 56° C. for 30 minutes. Serum for each animal and the standard serum are placed in at least two wells for each serum, and 2-fold serially diluted with MEM medium. In addition, the respective wells are inoculated to about 100 $CCID_{50}$ with neutralizing virus suspensions of the respective types. Next, all the plates are placed in a 36±1° C. $CO_2$ incubator for 3 hours, then allowed to react overnight at about 4° C. Cell suspension containing $1\times10^4$ cells is added the following day to each well, and is cultured in a 36±1° C. $CO_2$ incubator for 7 days. After the completion of culturing, the CPE for each well are examined, the serum dilution ratio at the time of 50% neutralization is calculated, and the reciprocal thereof is treated as the neutralizing antibody titer. From statistical treatment and comparison of the test results, the test specimen must have a potency equal to or higher than the control.

Results for the accelerated test are shown in Table 1. Lot 04C (Japan Polio Research Institute) was used as the control IPV.

TABLE 1

|  | Specification | At start of test | 1 month | 2 months | 3 months |
|---|---|---|---|---|---|
| Inactivated polio vaccine type I | Equal to or higher than control IPV | 1.7 | 1.7 | 1.5 | 2.1 |
| Inactivated polio vaccine type II | Equal to or higher than control IPV | 2.1 | 2.0 | 1.6 | 1.5 |
| Inactivated polio vaccine type III | Equal to or higher than control IPV | 20.3 | 12.3 | 5.9 | 6.0 |
| Precipitated pure pertussis vaccine | 8 units/mL | 15.8 | 13.8 | 14.6 | 27.3 |
| Precipitated diphtheria toxoid | 47 units/mL | 97.9 | 109.3 | 85.9 | 102.9 |
| Precipitated tetanus toxoid | 27 units/mL | 72.3 | 88.6 | 105.5 | 79.4 |

Example 10

Vero Cell Cultivation by Microcarrier Method, and Poliovirus Cultivation (i) Vero Cell Cultivation Cells that had been subcultured in a static culture starting from a working bank of Vero cells (MWCB93) were detached with a trypsin-EDTA solution (0.25% trypsin, 0.14 M EDTA), then centrifuged at 600 rpm for 10 minutes and subsequently suspended in a cell growth medium (Dulbecco's modified Eagle medium (DME) containing 5 vol % calf serum, 0.11% sodium bicarbonate ($NaHCO_3$), 0.1% fructose, 20 µg/mL erythromycin, and 100 µg/mL kanamycin).

A microcarrier (CYTODEX 1 (trade name) was swelled in PBS (−), autoclave sterilized at 121° C. for 15 minutes, then substituted with cell growth medium and used.

CELLIGEN Plus and CELLIGEN bioreactors manufactured by New Brunswick Scientific were used as the culture apparatuses. The microcarrier and cell suspension were added to the bioreactor, following which the cell growth medium was added to a final volume of 4.8 L (in the case of the CELLIGEN bioreactor, 3.5 L) and culturing was carried out at a temperature of 37.0° C., a dissolved oxygen concentration (DO) of 15%, a pH of 7.15 and a rotational speed of 35 to 50 rpm. Medium exchange using cell growth medium having a $NaHCO_3$ at the concentration of 0.15% as the exchange medium was carried out continuously from day 2 of culturing at a rate of about 4 L/day (in the case of the Celligen bioreactor, the entire amount of medium was exchanged once every other day). The cell count was measured using a COULTER COUNTER (trade name).

Figure 1:
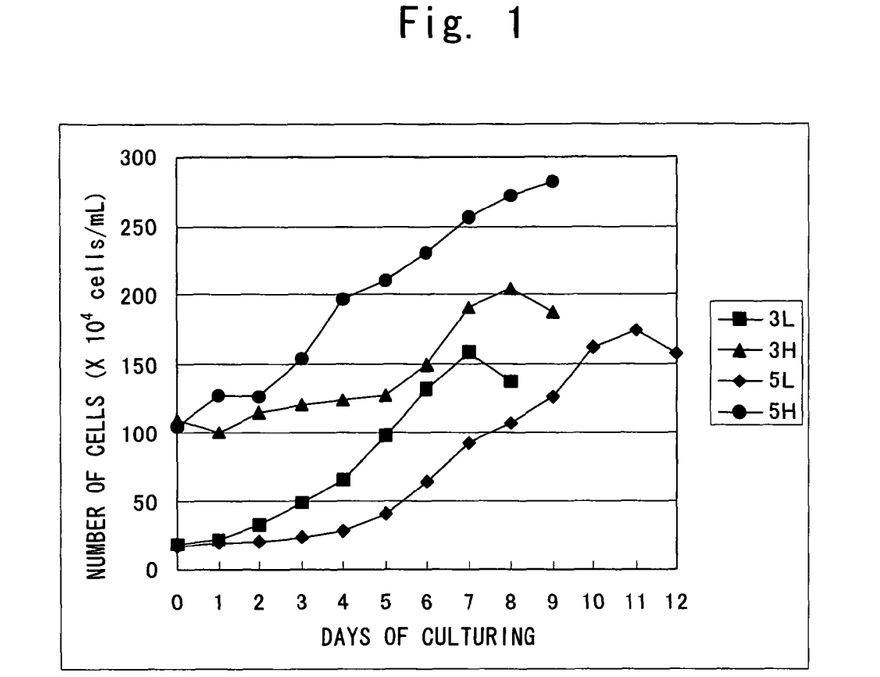
FIG. 1 is a graph showing Vero cell growth curves in the culturing of Vero cells by a microcarrier method. Here, "3L" indicates a starting cell number of about $2 \times 10^5$ cells/mL (low concentration) and 3 g/L of microcarrier. "3H" indicates a starting cell number of about $10 \times 10^5$ cells/mL (high concentration) and 3 g/L of microcarrier. "5L" indicates a starting cell number of about $2 \times 10^5$ cells/mL (low concentration) and 5 g/L of microcarrier. "5H" indicates a starting cell number of about $10 \times 10^5$ cells/mL (high concentration) and 5 g/L of microcarrier.

The cell culturing results are shown in FIG. 1 (Celligen bioreactors were used only in the 3H tests). At a carrier concentration of 3 g/L, the cell count reached a maximum on day 7 at a low-concentration starting cell number (3 L, about $2\times10^5$ cells/mL) and reached a maximum on day 8 at a high-concentration starting cell number (3H, about $10\times10^5$ cells/mL), after which it decreased. At a carrier concentration of 5 g/L, the cell count increased over a period of 11 days at a low-concentration starting cell number (5 L, about $2\times10^5$ cells/mL), but the cell count decreased on day 12. In the case of a low-concentration starting cell number, the total cell count at a carrier concentration of 5 g/L was greater on day 10 than the total cell count at a carrier level of 3 g/L, but the difference was not large. At a carrier concentration of 5 g/L and a high-concentration starting cell number (5H, about $10\times10^5$ cells/mL), the cell count was still increasing on day 9, with the cell count at that point being about $2.8\times10^6$ cells/mL, representing an increase of about 2.7 times over the starting cell number.

(ii) Culturing of Poliovirus

A type I poliovirus (IS-90C) was used as the seed virus. On the final day of cell count measurements, the cells were washed with a 4-fold volume (based on culturing capacity of bioreactor) of EBSS containing 0.075% $NaHCO_3$. The seed virus was then diluted in 1 liter of M-199 (E) medium containing 0.3% $NaHCO_3$, 20 µg/mL erythromycin and 100 µg/mL kanamycin (virus growth medium). The resulting virus dilution was then inoculated into the washed cells, and the virus culture medium was added up to the culturing capacities of the respective bioreactors. Virus cultivation was carried out at a culturing temperature of 33.3° C., 15% dissolved oxygen (DO), a pH of 7.40 and a rotational speed of 35 to 50 rpm. Virus cultivation was stopped when the cells had completely detached from the microcarrier due to the cytopathic effects (CPE) of the virus, at which point the virus fluid was harvested. The harvested virus fluid was cryopreserved at −80° C.

In this test, virus cultivation was begun on the final day of measurement on the respective cell growth curves shown in FIG. 1.

Measurement of the virus titer was carried out as follows. GMK-2 cells cultured for 3 days in a roller tube were washed twice with 1 mL of HBSS containing 0.075% $NaHCO_3$, 200 u/mL penicillin and 200 µg/mL streptomycin, following which 1 mL of a cell maintenance fluid (M-199 medium containing 0.1% bovine serum albumin, 0.225% $NaHCO_3$, 200 u/mL penicillin and 200 µg/mL streptomycin) was added. The test virus fluid was serially diluted 0.5 $\log_{10}$ with the cell maintenance fluid, and 0.2 mL of $10^{-7}$ to $10^{-8.5}$ virus fluid per tube was inoculated in 5 tubes at each dilution level. Following inoculation, culturing was carried out for 7 days in a 36° C. incubator. The infectivity titer ($CCID_{50}$/0.2 mL) was computed by the Reed & Muench method based on a judgment from observation of the cytopathic effects (CPE) on day 7.

Figure 2:
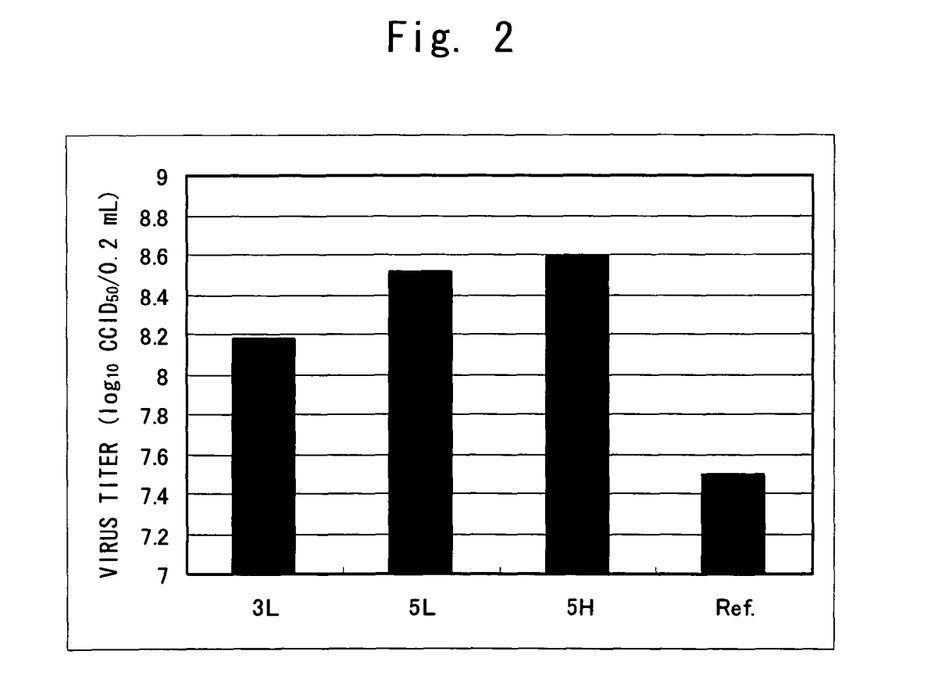
FIG. 2 is a graph showing the infectivity titers (virus titers) of poliovirus type I obtained in Vero cells cultured under various conditions. Here, "3L" represents type I polioviruses obtained in Vero cells cultured from a starting cell number of about $2 \times 10^5$ cells/mL (low concentration) on 3 g/L of microcarrier. "5L" indicates type I polioviruses obtained in Vero cells cultured from a starting cell number of about $2 \times 10^5$ cells/mL (low concentration) on 5 g/L of microcarrier. "5H" indicates type I polioviruses obtained in Vero cells cultured from a starting cell number of about $10 \times 10^5$ cells/mL (high concentration) on 5 g/L of microcarrier. "Ref." indicates type I polioviruses grown using green monkey kidney cells.

FIG. 2 shows the infectivity titers (virus titers) of type I poliovirus obtained in the Vero cells cultured under various conditions. As a result of virus cultivation, the highest infectivity titer was obtained in the system having a carrier concentration of 5 g/L and a high-concentration starting cell number (5H); this system reached a cell density on day 9 of $2.8\times10^6$ cells/mL. The systems, arranged according to the size of the infectivity titers thereof in descending order, were 5H, 5L and 3L. These results were in agreement with the total cell counts. In addition, compared with the virus fluid obtained by cultivation in green monkey kidney cells as the control, an infectivity titer more than 10 times higher was obtained in the 5H system. The virus titers shown in FIG. 2 ($\log_{10} CCID_{50}$/0.2 mL) were 8.18 in the 3L system, 8.51 in the 5L system, 8.59 in the 5H system, and 7.50 in Ref (control).

INDUSTRIAL APPLICABILITY

High-potency Sabin strains of polioviruses can be obtained by culturing, in the presence of from about 4 g/L to about 6 g/L of a microcarrier, Vero cells inoculated with Sabin strain polioviruses. Inactivated Sabin strain polioviruses can be efficiently produced by using high-potency Sabin strain polioviruses. Therefore, a process for producing a combined vaccine which includes the step of culturing, in the presence of from about 4 g/L to about 6 g/L of microcarrier, Vero cells inoculated with Sabin strain polioviruses (the production process of the present invention) is useful as a process for efficiently producing combined vaccines containing inactivated Sabin strain polioviruses. In addition, because the combined vaccine of the present invention is capable of effectively suppressing the onset of polio, pertussis, diphtheria and tetanus, it is useful as a vaccine for polio, pertussis, diphtheria and tetanus.

The invention claimed is:

1. A process for producing a combined vaccine containing,
   (A) type I, type II, and type III inactivated Sabin strains of poliovirus in a weight proportion of D antigens of (2-4):(80-120):(80-120),
   (B) a *Bordetella pertussis* protective antigen,
   (C) a diphtheria toxoid, and
   (D) a tetanus toxoid,
   the process comprising:
   (a) culturing Vero cells in about 4 g/L to about 6 g/L of a microcarrier, wherein the culture medium is selected from the group consisting of ME medium, DME medium, RPMI 1640 medium and RPMI 199 medium, and wherein the culture medium contains from about 5 to about 70 vol % of calf serum or fetal bovine serum;
   (b) infecting the Vero cells with type I, type II and type III Sabin strains of poliovirus;
   (c) allowing the Sabin strains to proliferate;
   (d) recovering a virus fluid containing the Sabin strains;
   (e) inactivating the Sabin strains to produce the type I, type II, and type III inactivated Sabin strains of poliovirus of (A); and
   (f) mixing the inactivated Sabin strains of poliovirus of (A) with a diphtheria-tetanus-pertussis combined vaccine comprising the *Bordetella pertussis* protective antigen, diphtheria toxoid, and tetanus toxoid of (B)-(D).

2. The process according to claim 1, wherein the microcarrier has a concentration of about 5 g/L.

3. The process according to claim 1, wherein the microcarrier is a dextran microcarrier.

4. The process according to claim 1, wherein the step of culturing the Vero cell (step (a)) is carried out on a scale of at least about 3 liters.

5. The process according to claim 1, wherein the step of culturing the Vero cell (step (a)) is carried out on a scale of at least about 30 liters.

6. The process according to claim 1, further comprising (d-2) a step of purifying the virus fluid.

7. The process according to claim 6, wherein the purifying step (step (d-2)) comprises:
   (i) forming the virus fluid recovered in step (d) into a pellet by ultracentrifugation,
   (ii) sonicating a re-suspension of the pellet; and
   (iii) purifying by column chromatography.

8. The process according to claim 7, wherein the purification by column chromatography (iii) is carried out one time only.

9. A vaccine produced by the process according to claim 1.

10. The process according to claim 1, wherein the microcarrier has a concentration of about 4.5 g/L to about 5.5 g/L.

* * * * *

UNITED STATES PATENT AND TRADEMARK OFFICE
CERTIFICATE OF CORRECTION

PATENT NO.      : 8,753,646 B2
APPLICATION NO. : 12/311365
DATED           : June 17, 2014
INVENTOR(S)     : Shinobu Abe et al.

It is certified that error appears in the above-identified patent and that said Letters Patent is hereby corrected as shown below:

In The Specification

Col. 7, line 23, and Col. 13, line 52, "100,000 g" should be --100,000g--.

Col. 11, line 34, "Sodium edetate-2Na.2H$_2$0" should be --Sodium edetate-2Na · 2H$_2$0--.

Col. 11, line 43, "Na$_2$HPO$_4$.12H$_2$0" should be --Na$_2$HPO$_4$ · 12H20--.

Col. 13, line 20, "about $10^{-1}$" should be --about $10^{-3}$--.

In The Claims

Col. 21, claim 1, line 33, "about 70 vol %" should be --about 20 vol %--.

Col. 21, claim 1, line 34, "type II and" should be --type II, and--.

Col. 22, claim 1, line 5, "(A" should be --(A)--.

Signed and Sealed this
Thirteenth Day of January, 2015

Michelle K. Lee
*Deputy Director of the United States Patent and Trademark Office*

UNITED STATES PATENT AND TRADEMARK OFFICE
CERTIFICATE OF CORRECTION

PATENT NO. : 8,753,646 B2  
APPLICATION NO. : 12/311365  
DATED : June 17, 2014  
INVENTOR(S) : Shinobu Abe et al.

It is certified that error appears in the above-identified patent and that said Letters Patent is hereby corrected as shown below:

In The Specification

Col. 7, line 23, and Col. 13, line 52, "100,000 g" should be --100,000g--.

Col. 11, line 34, "Sodium edetate-2Na.2H$_2$0" should be --Sodium edetate-2Na · 2H$_2$0--.

Col. 11, line 43, "Na$_2$HPO$_4$.12H$_2$0" should be --Na$_2$HPO$_4$ · 12H$_2$0--.

Col. 13, line 20, "about $10^{-1}$" should be --about $10^{-3}$--.

In The Claims

Col. 21, claim 1, line 33, "about 70 vol %" should be --about 20 vol %--.

Col. 21, claim 1, line 34, "type II and" should be --type II, and--.

Col. 22, claim 1, line 5, "(A" should be --(A)--.

This certificate supersedes the Certificate of Correction issued January 13, 2015.

Signed and Sealed this  
Seventeenth Day of February, 2015

Michelle K. Lee  
*Deputy Director of the United States Patent and Trademark Office*

UNITED STATES PATENT AND TRADEMARK OFFICE
CERTIFICATE OF CORRECTION

PATENT NO.         : 8,753,646 B2
APPLICATION NO.    : 12/311365
DATED              : June 17, 2014
INVENTOR(S)        : Shinobu Abe and Bunshichi Simizu

Page 1 of 1

It is certified that error appears in the above-identified patent and that said Letters Patent is hereby corrected as shown below:

In the claims

Col. 21, claim 1, line 31, "and RPMI 199 medium" should be -- and 199 medium --.

Signed and Sealed this
Fifth Day of April, 2016

Michelle K. Lee
*Director of the United States Patent and Trademark Office*